United States Patent [19]
Agrawal et al.

[11] Patent Number: 5,541,306
[45] Date of Patent: Jul. 30, 1996

[54] AMINOALKYLPHOSPHOTRIESTER OLIGONUCLEOTIDE DERIVATIVES

[75] Inventors: Sudhir Agrawal; Jin-Yan Tang, both of Shrewsbury, Mass.

[73] Assignee: Worcester Foundation for Biomedical Research, Shrewsbury, Mass.

[21] Appl. No.: 357,666

[22] Filed: Dec. 16, 1994

Related U.S. Application Data

[60] Division of Ser. No. 206,175, Mar. 3, 1994, which is a continuation-in-part of Ser. No. 490,481, Mar. 8, 1990, Pat. No. 5,321,131.

[51] Int. Cl.$^6$ .................. C07H 21/00; C07H 21/02; C07H 21/04; C12Q 1/68
[52] U.S. Cl. .................. 536/22.1; 435/6; 536/24.3; 536/25.33; 536/25.6; 536/26.5; 536/26.6
[58] Field of Search .................. 536/24.3, 25.33, 536/26.5, 25.6, 26.6, 22.1; 435/6

[56] References Cited

U.S. PATENT DOCUMENTS

| | | | |
|---|---|---|---|
| 4,762,779 | 8/1988 | Snitman | 435/6 |
| 4,959,463 | 9/1990 | Froehler et al. | 536/27 |
| 4,965,349 | 10/1990 | Woo et al. | 536/27 |

OTHER PUBLICATIONS

Haralambidis et al. (1990) *Nucleic Acids Res.* 18:493–499.
Haralambidis et al. (1990) *Nucleic Acids Res.* 18:501–505.
Agrawal et al. (1989) *Tetrahedron Letters* 30(50):7025–7028.
Fidanza et al. (1989) *J. Am. Chem. Soc.* 111:9117–9119.
Helene & Toulme, (1989) *Oligonucleoides* (Cohen, ed.) MacMillan Press, pp. 137–167.
Nelson et al. (1989) *Nucleic Acids Res.* 17:7187–7194.
Agrawal et al. (1988) *Proc. Natl. Acad. Sci.* (USA) 85:7079–7083.
Agrawal et al. (1988) *J. Cell Biology* 107:468.
Cardullo et al. (1988) *Proc. Natl. Acad. Sci.* (USA) 85:8790–8794.
Froehler et al. (1988) *Nucleic Acids Res.* 16:4831–4839.
Jager et al. (1988) *Biochemistry* 27:7237–7246.
Letsinger et al. (1988) *J. Am. Chem. Soc.* 110:4470–4471.
Matthews et al. (1988) *Analytical Biochem.* 169:1–25.
Agrawal et al. (1987) *Tetrahedron Letters* 28(31)3539–3542.
Caruthers et al. (1987) *Methods in Enzymology* 154:287–313.
Le Doan et al. (1987) *Nucleic Acids Res.* 15:8643–8659.
Agrawal et al. (1986) *Nucleic Acids Res.* 14:6227–6245.
Nevinski et al. (1983) *Chemical Abstracts* 99(5):35059 (Aug. 1, 1993).
Dobranravova et al. (1983) *Chemical Abstracts* 98(7):54383 (Feb. 14,1983).
Zwierzak A. (Aug. 1975) *Synthesis International Journal of Methods in Synthetic Organic Chemistry* "Communications" pp. 507–509.
Uhlmann et al. Chemical Reviews 90(4):544–584, 1990.

*Primary Examiner*—W. Gray Jones
*Assistant Examiner*—Paul B. Tran
*Attorney, Agent, or Firm*—Lappin & Kusmer

[57] ABSTRACT

Disclosed are methods of producing a synthetic oligonucleotide of selected nucleotide sequence which is internally functionalized at least one selected location with an aminoalkylphosphotriester, and labelled with a nonradioactive material. Also disclosed are oligonucleotides produced by this method.

2 Claims, 2 Drawing Sheets

AMINOALKYLPHOSPHOTRIESTER OLIGONUCLEOTIDE DERIVATIVES

CROSS-REFERENCE TO RELATED APPLICATIONS

This is a divisional application of Ser. No. 08/206,175, filed Mar. 3, 1994, which is a continuation-in-part of applicant's application Ser. No. 07/490,481, entitled "SITE-SPECIFIC FUNCTIONALIZATION OF OLIGODEOXY-NUCLEOTIDES FOR NON-RADIOACTIVE LABELLING", filed Mar. 8, 1990 (now U.S. Pat. No. 5,321,131, issued Jun. 14, 1994).

FUNDING

Work described herein was supported by Cooperative Grant U01 124846 from the National Institute of Allergies and Infectious Disease and a grant from the G. Harold and Leila Y. Mathers Foundation.

BACKGROUND OF THE INVENTION

There is at present growing interest in non-radioactively labelled modified oligode. oxynucleotides. Biotin (Agrawal et al. (1986) *Nucl. Acids Res.* 14:6227–6245; Agrawal (1989) *Tet. Lett.* 30: 7025–7028), florophores (Cardullo et al. (1988) *Proc. Natl. Acad. Sci.* (USA) 85: 8790–8794; Agrawal et al. (1988) *J. Cell Biology* 107:468; Haralambidis et 0al. (1989) *Nucl. Acids Res.* 18(3) :501–505), intercalating (Helene et al. *Oligodeoxynucleotides—Antisense Inhibitors of Gene Expression* (Cohen, ed.) Macmillan Press (1989) pp.137–166) and chelating reagents (Oser et al. (1988) *Nucl. Acids Res.* 16:1181–1196) attached to synthetic oligonucleotides are becoming important tools of molecular biology. A variety of enzymatic and chemical procedures have been developed for their synthesis (Matthews et al. (1988) *Anal. Biochem.* 169: 1–25). Central to some of these procedures are (a) the introduction of a reactive group at either the 3'- or 5'- terminus of the oligonucleotide (Agrawal et al. (1986) *Nucl. Acids Res.* 14:6227–6245; Agrawal (1989) *Tet. Lett.* 30:7025–7028; Fidanza et al. (1989) *J. Am. Chem. Soc.* 111: 9117–9119; Nelson (1989) *Nucl. Acids Res.* 17:7187–7194 or (b) the synthesis of modified nucleosides which contain the masked reactive group and are incorporated into the nucleic acid (Fidanza et al. (1989) *J. Am. Chem. Soc.* 111: 9117–9119). The presently-available methods are useful, but are limited in their usefulness for site specific internal non-radioactive labelling of synthetic oligonucleotides.

SUMMARY OF THE INVENTION

The present invention relates to compounds consisting of a plurality of nucleosides including adenosine, thymidine, cytidine, guanosine, and uridine, which are covalently linked by at least one aminoalkylphosphoramidate, aminoalkylphosphotriester, or aminoalkylphosphorothioamidate residue. As used herein the terms "adenosine," "thymidine," "cytodine," and "guanosine" are intended to include the ribose and deoxyribose forms of these nucleosides.

The present invention also relates to a method of site specific functionalization of oligonucleotides of any sequence, length, or having any internucleotide linkage for non-radioactive labelling, as well as to the functionalized oligonucleotides and non-radioactively labelled oligonucleotides produced by the method. This method makes it possible to modify one or more selected internucleoside phosphate (s) in a synthetic oligonucleotide in such a manner that it (they) can be used to incorporate a non-radioactive material into the molecule. In particular, the method of the present invention is used to modify one or more selected internucleoside phosphates in a synthetic oligodeoxynucleotide, oligoribonucleotide, or oligonucleotide containing both deoxyribonucleotides and ribonucleotides, to give aminoalkylphosphoramidate, aminoalkylphosphotriester, or aminoalkylphosphorothioamidate residues. The amino group(s) of the resulting modified residue(s) then further react with a non-radioactive label, such as biotin, fluorescein, or rhodamine (e.g., N-hydroxysuccinimide ester of biotin, N-caproyl amidobiotin, and a variety of fluorophore isothiocyantes), or derivatives thereof, to produce a non-radioactively labelled oligonucleotide in which the label is present at a predetermined location or locations.

In one embodiment the present method, an H-phosphonate internucleoside linkage is oxidized with an appropriately protected diamine, such as N-1-trifluoroacetylhexanediamine ($CF_3CONH(CH_2)_6NH_2$), N-1-trifluoroacetylpentanediamine ($CF_3CONH(CH_2)_5NH_2$), N-1-trifluoroacetylbutyldiamine ($CF_3CONH(CH_2)_4NH_2$), N-1-trifluoroacetylpropyldiamine ($CF_3CONH(CH_2)_3NH_2$), or N-1-trifluoroacetylethyldiamine ($CF_3CONH(CH_2)_2NH_2$), in the presence of an appropriate solvent, such as carbon tetrachloride, to give a phosphoramidate or phosphorothioamidate internucleoside linkage (Zwierzak (1975) *Synthesis* pp. 507–508; Froehler et al. (1989) *Nucl. Acids Res.* 16: 4831–4839; Letsinger et al. (1988) *J. Am. Chem. Soc.* 110:4470–4471; Agrawal et al. (1988) *Proc. Natl. Acad. Sci.* (USA) 85:7079–7083; Jager et al. (1988) *Biochem.* 27: 7237–7246). Alternatively, the H-phosphonate internucleoside linkage is oxidized to give a phosphotriester internucleoside linkage with an appropriately protected aminoalkyl alcohol in N-methylimidazole-triethylamine-carbontetrachloride. The resulting phosphoramidate, phosphotriester, or phosphorothioamidate internucleoside linkage is stable under oligonucleotide assembly conditions using phosphoramidite chemistry (Caruthers et al. (1987) *Meth. Enzymol.* 154:287–313) and subsequent deprotection steps.

The methods of the invention are used to produce non-radioactively labelled oligonucleotides which include a non-radioactive material at one or more sites and are useful in research and in the diagnosis and treatment of diseases and conditions of interest.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1B:
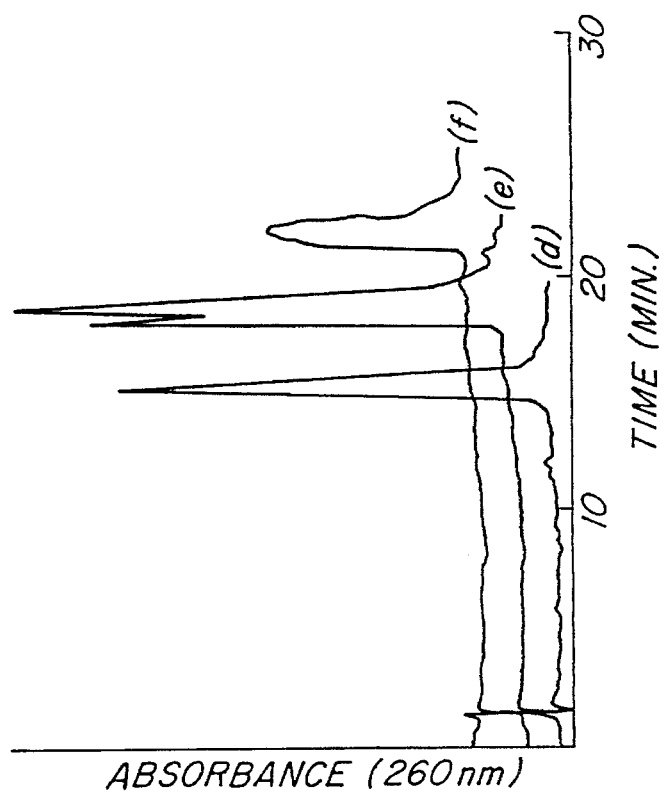
FIG. 1B is a graphic representation of the results of reversed phase HPLC of ion exchange purified oligomers 1 (chromatograph (d)), 2 (chromatograph (e)), and 3 (chromatograph (f))

The patent and scientific literature referred to herein establishes the knowledge that is available to those with skill in the art. The issued U.S. patent and allowed applications cited herein are hereby incorporated by reference.

The present invention relates to a method of producing oligonucleotides which have a desired (selected) nucleotide sequence and which are labelled internally with a non-radioactive material or reporter group at one or more internucleoside linkages. In the method of the present invention, one or more selected internucleoside phosphate residues are modified to produce aminoalkylphosphoramidate, aminoalkylphosphotriester, or aminoalkylphosphorothioamidate residues which are present in an oligonucleotide at all or any number of selected positions. The amino group(s) in such modified (i.e., functionalized) residues is further reacted with a label or reporter group, resulting in production of a non-radioactively labelled oligonucleotide labelled internally at selected location(s).

Briefly, the present method is carried out by oxidizing an H-phosphonate internucleoside linkage using an appropriately protected diamine or amino alcohol represented by the formulae $YNH(CH_2)_nNH_2$, $YNH(CH_2)_nOH$, in which "Y" is a base labile protecting group and "n" can be 2 or more. For example, an H-phosphate internucleoside is oxidized using N-1-trifluoroacetylethyldiamine $(CF_3CONH(CH_2)_2NH_2)$, N-1-trifluoroacetylpropyldiamine $(CF_3CONH(CH_2)_3NH_2)$, N-1-trifluoroacetylbutyldiamine $(CF_3CONH(CH_2)_4NH_2)$, N-1-trifluoroacetylpentanediamine $(CF_3CONH(CH_2)_5NH_2)$, or N-1-trifluoroacetylhexanediamine pentane $(CF_3CONH(CH_2)_6NH_2)$, in the presence of an appropriate solvent such as anhydrous carbon tetrachloride. As a result, a primary aliphatic amine is incorporated at the internucleoside phosphate as a phosphoramidate.

In the case of phosphotriester linkages, oxidation is carried out using a suitably protected amino alcohol, represented by the formula $YNH(CH_2)_nOH$, in which "Y" is a base labile protecting group and "n" can be 2 or more. For example, an H-phosphonate internucleoside linkage is oxidized using FMOC—NH$(CH_2)_2$OH, FMOC—NH$(CH_2)_3$OH, FMOC—NH$(CH_2)_4$OH, FMOC—NH$(CH_2)_5$OH, or N-1-fluoroenylmethyoxycarbonylaminohexanol (pentanol) (FMOC—NH$(CH_2)_6$OH) in the presence of N-methylimidazole-triethylamine-carbon tetrachloride (at, e.g., 5:5:90).

In the case of aminoalkylphosphorothioamidate linkages, oxidation is carried out using a suitably protected diamine as described above.

The remaining nucleotides needed to produce the desired nucleotide sequence are covalently added using art-recognized techniques, such as phosphoramidite, H-phosphonate chemistry, or methyl phosphoramidite chemistry (see, e.g., Uhlmann et al. (1990) Chem. Rev. 90:543–584; Agrawal et al. (1987) Tet. Lett. 28: (31) :3539–3542); Caruthers et al. (1987) Meth. Enzymol. 154: 287–313; copending U. S. patent application Ser. No. 07/334,679 ("METHOD OF SYNTHESIZING OLIGONUCLEOTIDES AND THEIR ANALOGS ADAPTABLE TO LARGE SCALE SYNTHESIS," by S. Agrawal and P. Zamecnik, filed Apr. 6, 1989). After the desired oligonucleotide is produced, the protecting group present on the primary aliphatic amine or amino alcohol is removed. The unmasked amino group can now react with one or more selected labels or reporter groups. As a result, the oligonucleotide is non-radioactively labelled at one or more selected internal locations. One or both amino groups present in the diamine react with the selected label.

The methods of the present invention are represented in three sets of steps below. The following is an explanation of those steps, with reference to the respective reactants and steps represented below.

METHOD 1

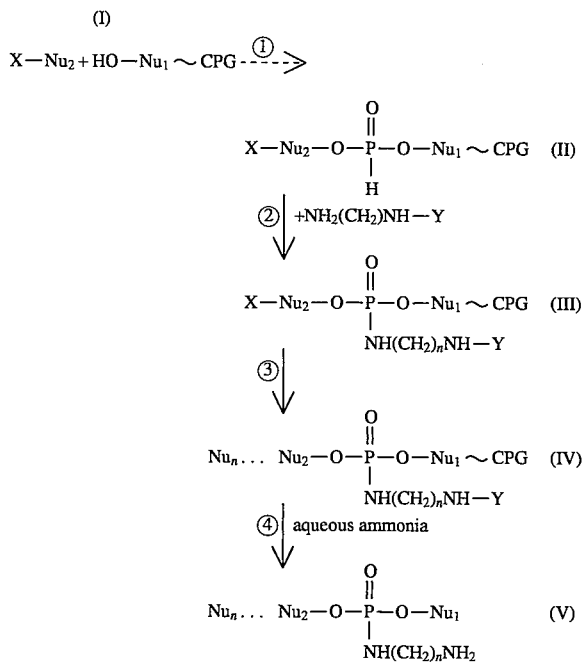

METHOD 2

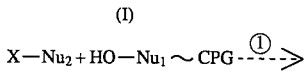

-continued

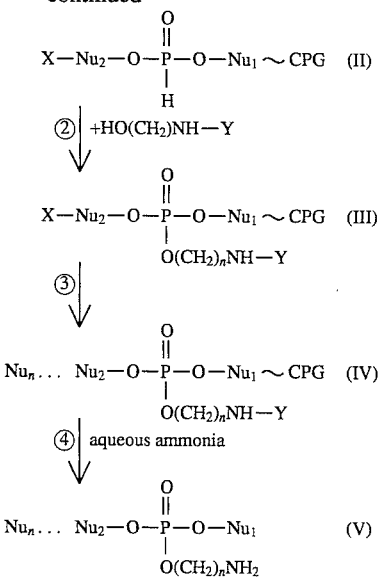

METHOD 3

(I)

X—Nu₂+HO—Nu₁∼CPG

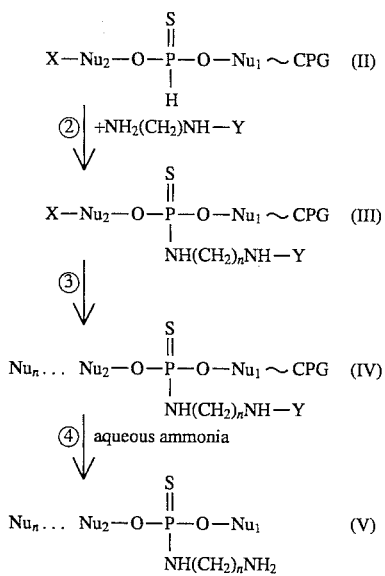

In Step 1 of the three methods above, initial coupling of two nucleotides (designated $Nu_1$ and $Nu_2$) is carried out using H-phosphonate chemistry. Generally, $Nu_1$ is bound to a solid support, such as CPG, and terminates in a dimethoxytrityl residue (designated (I)). As a result, a support-bound dinucleoside H-phosphonate (II) is produced.

In Step 2, the support-bound dinucleoside H-phosphonate (II) is subsequently oxidized by being combined with an appropriately protected diamine or amino alcohol, in the presence of a suitable solvent, resulting in formation of a phosphoramidate, phosphotriester, or phosphorothioamidate internucleoside linkage and linking of the protected diamine or aminoalcohol, to the dinucleoside through the unprotected amino group of the diamine or amino alcohol. The resulting product is designated (III).

Then, in Step 3, the dimethoxytrityl residue present on the unbound end of (I) is removed and the remaining nucleotides (e.g., $Nu_3$, $Nu_4$, and so on up to $Nu_n$) of the desired oligonucleotide to be produced are covalently added at the now free end, using phosphoramidite, H-phosphonate, or some other chemistry, producing a support-bound oligonucleotide (IV) which includes the phosphoramidate, phosphotriester, or phosphorothioamidate linkage produced in Step 2.

In Step 4, the protecting group "Y" present on the diamine is removed and the compound is removed from the solid support. This results in production of an unbound functionalized oligonucleotide (V) (i.e., an aminoaliphatic oligomer or an oligonucleotide having a desired nucleotide sequence and an alkylamino group present at the selected internucleoside phosphate(s) as a phosphoramidate, phosphotriester, or phosphorothioamidate.

In Step 5, the unbound functionalized oligonucleotide is reacted with an appropriate form of a non-radioactive material, which becomes bound to the amino group and serves as a label or reporter group on the oligonucleotide. This results in production of an oligonucleotide labelled site specifically with a non-radioactive material. The non-radioactive material can be a fluorophore, chemiluminescent tag, spin label, enzyme, chelator, heterocyclic molecule, protein, lipid, drug derivative, antigen, an intercalator, or other organic or inorganic moiety.

It is possible, using the present method, to produce oligonucleotides of desired sequence which are labelled internally at one or more nucleosides. The oligonucleotide backbone can be unmodified (e.g., as it occurs in nature, i.e., phosphodiester) or modified (e.g., amidate, alkylphosphate, phosphothioate, phosphodithioate, phosphate ester, phosphotriester, carbamate, carboxy methyl ester, or carbonate acetamidate containing backbones). The label present at two or more sites can be the same (e.g., biotin) or different, and can be present at as many sites as desired. As described in the EXAMPLES below, an oligomer of any sequence can be produced, functionalized at a selected site or sites, and labelled at the site(s) with a non-radioactive material.

In the above description of the present method, two single nucleotides (designated $Nu_1$ and $Nu_2$) are initially joined using H-phosphonate chemistry and the resulting oligonucleotide is functionalized at the internucleoside phosphate linkage formed between $Nu_1$ and $Nu_2$. However, any number of nucleotides can be joined, using art-recognized techniques such as H-phosphonate chemistry, before modification of a selected internucleoside phosphate linkage is carried out.

For example, a 5mer, 17mer, 25mer, and 50mer functionalized at a single internal site, at two internal sites, at three contiguous or non-contiguous internal sites, and at multiple non-contiguous and contiguous sites can be produced by the method of the invention. Using H-phosphonate chemistry, for example, an internal nucleotide 1 (e.g., a support-bound nucleotide such as $Nu_1$) can be added to, resulting in production of a longer sequence (e.g., $Nu_{10}Nu_9 \ldots Nu_1$). The longer sequence can then be functionalized by the method described above, resulting in production of a functionalized oligonucleotide (e.g., $Nu_{10}\downarrow Nu_9 \ldots Nu_1$, in which the internucleoside phosphate linkage between $Nu_9$ and $Nu_{10}$ is modified). The modified oligonucleotide can then be further elongated by addition of selected nucleotides to produce a modified oligonucleotide of desired sequence (e.g., $Nu_n \ldots Nu_{10}, \downarrow Nu_9 \ldots Nu_1$).

The protecting group present can be removed as described above. Alternatively, the functionalized oligonucleotide initially produced can be extended (by addition of selected nucleotides), and one or more additional internucleoside phosphate linkages can be modified, thereby producing a functionalized oligonucleotide which has two or more sites at which non-radioactive material can be added.

Protecting groups other than trifluoroacetyl (—CO—CF$_3$), as described above, can also be used to protect the diamine or amino alcohol. Other base labile protecting groups, such as FMOC and TBOC, may also be used. The linker present between the two amino groups in the diamine used can be of any suitable length (e.g., —(CH$_2$)$_2$— to —(CH$_2$)$_n$—), preferably from about 2 to about 6 carbon atoms; the length used in a particular case can be determined empirically. The diamine can be branched or unbranched and bi-functional or multifunctional.

Assessment of the functionalized oligomers made by the method of the invention can be carried out, for example, by analytical high performance liquid chromatography (HPLC), reversed phase HPLC, and high performance capillary electrophoresis (HPCE).

The following examples illustrate the preferred modes of making and practicing the present invention, but are not meant to limit the scope of the invention since alternative methods may be utilized to obtain similar results.

EXAMPLES

1. Preparation of Oxidizing Agents

N-1-trifluoroacetylhexanediamine, (CF$_3$CONH(CH$_2$)$_6$NH$_2$) is prepared by adding ethyltrifluoroacetate (1.2 ml, 10 mmol) dropwise over one hour to a stirred mixture of hexanediamine (1.16 g; 10 mmol) and triethylamine (1 ml; 7 mmol) in 20 ml methanol. The solution is stirred overnight. After removal of solvents, the reaction mixture is flash chromatographed on silica using 0–25% methanol in dichloromethane. The fractions containing the desired product are pooled and concentrated to give a colorless product.

N-1-trifluoroacetylpropyldiamine (CFCONH(CH$_2$)$_3$NH$_2$) is prepared by adding ethyltrifluoroacetate (1.2 ml, 10 mmol) dropwise over one hour to a stirred mixture of 1,3-diaminopropane (0.74 g; 10 mmol) and triethylamine (1 ml; 7 mmol) in 20 ml methanol. The solution is stirred overnight. After removal of solvents, the reaction mixture is flash chromatographed on silica using 0–25% methanol in dichloromethane. The fractions containing the desired product are pooled and concentrated to give a colorless product.

N-1-trifluoroacetylbutyldiamine (CFCONH(CH$_2$)$_4$NH$_2$) is prepared by adding ethyltrifluoroacetate (1.2 ml, 10 mmol) dropwise over one hour to a stirred mixture of 1,4-diaminobutane (0.88 g; 10 mmol) and triethylamine (1 ml; 7 mmol) in 20 ml methanol. The solution is stirred overnight. After removal of solvents, the reaction mixture is flash chromatographed on silica using 0–25% methanol in dichloromethane. The fractions containing the desired product are pooled and concentrated to give a colorless product.

N-1-trifluoroacetylpentanediamine (CFCONH(CH$_2$)$_5$NH$_3$) is prepared by adding ethyltrifluoroacetate (1.2 ml, 10 mmol) dropwise over one hour to a stirred mixture of 1,5-diaminopentane (1.02 g; 10 mmol) and triethylamine (1 ml; 7 mmol) in 20 ml methanol. The solution is stirred overnight. After removal of solvents, the reaction mixture is flash chromatographed on silica using 0–25% methanol in dichloromethane. The fractions containing the desired product are pooled and concentrated to give a colorless product.

2. Preparation of Oligonucleotides to be Functionalized

Three 5mers, three 17mers, three 25mers, and three 50mers, each having a different nucleotide sequence, are prepared using H-phosphonate chemistry as described in Uhlmann et al. (*Chem. Rev.* (1990) 90:534–583). These oligomers are listed in TABLE 1.

TABLE 1

| SEQUENCE | SEQ ID NO: |
|---|---|
| AAATG | 1 |
| CGGCA | 2 |
| UGCCA | 3 |
| GTAAAACGACGGCCAGT | 4 |
| GTATTCAAAGGAGTACC | 5 |
| GAGCAUCACGGUGAGCG | 6 |
| CTCTCGCACCCATCTCTCTCCTTCT | 7 |
| GAATGACTGATTGAGTGACTGAATG | 8 |
| CAGUGACUGACUGAGCGACUGAACU | 9 |
| CGATGCGTAGGCCTAGAACTGGACTTACACTGGGATGCAAGTCAGCTGAT | 10 |
| TCAGTCGAGAGCTCGAGCTCGAGCGCTAGCGATGCAGTGCGATCGATAGC | 11 |
| AGCGCACUAGGCAAGUCCGCGAGAUCCACGAGCCAAUACGGACUCGCAGA | 12 |

0–25% methanol in dichloromethane. The fractions containing the desired product are pooled and concentrated to give a colorless powder (1.1 gm, yield-42.6%); melting point 52° C; $^1$H NMR (CDCl$_3$, d, TMS=) .00) 7.1–7.2 (m, 3H, NH$_2$, NH) 3.2–3.3 (m, 2H, CO—NH—CH$_2$), 2.8–2.9 (m 2 H, CH$_2$—NH$_2$) 1.2–1.6 (m, 8H,—CH—(CH$_2$)$_2$—CH$_2$—).

N-1-trifluoroacetylethyldiamine (CF$_3$CONH(CH$_2$)$_2$NH$_2$ is prepared by adding ethyltrifluoroacetate (1.2 ml, 10 mmol) dropwise over one hour to a stirred mixture of ethylenediamine (0.6 g; 10 mmol) and triethylamine (1 ml; 7 mmol) in 20 ml methanol. The solution is stirred overnight. After removal of solvents, the reaction mixture is flash chromatographed on silica using 0–25% methanol in dichlo- These same oligomers are also prepared with, in addition to the aminoalkyltriester, aminoalkylphosphoramidate, and/or aminoalkylphosphorothioamidate linkages, at least one nonfunctionalized, nonphosphodiester internucleotide linkages including a phosphorothioate, phosphorodithioate, phosphoramidate, alkylphosphonate, alkylphosphorothioate, and carbamate linkages at selected positions using the procedures described in Uhlmann et al. *Chem. Rev.* (1990) 90:534–583).

03. Functionalization

The following steps are carried out to produce a non-radioactively labelled oligonucleotide with a functionalized phosphoramidate:

METHOD 1

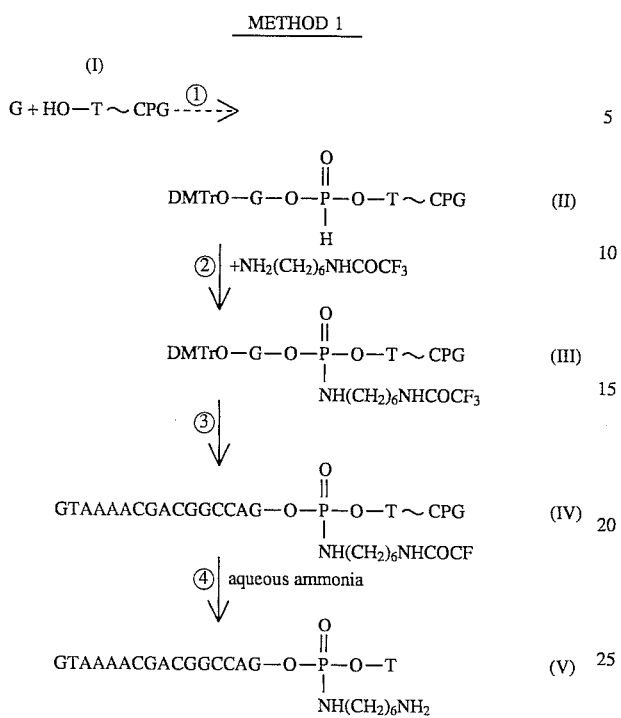

1. Initially, thymidine (T) ($Nu_1$) and protected deoxyguanosine H-phosphonate (G) ($Nu_2$) (I) are coupled using art-recognized H-phosphonate chemistry, resulting in production of a support-bound dinucleoside H-phosphonate (II).

2. The support-bound dinucleoside H-phosphonate (II) is oxidized using 4% N-1-trifluoroacetyldiaminohexane ($NH_2(CH_2)_6NH—CO—CF_3$) in carbon tetrachloride-dioxane (8:2, volume/volume) for 30 minutes, resulting in formation of a phosphoramidate internucleoside linkage between $Nu_2$ and $Nu_1$ (III). In other tests, oxidation is carried out using $CF_3CONH(CH_2)_2NH_2$, $CF_3CONH(CH_2)_3NH_2$, $CF_3CONH(CH_2)_4NH_2$, or $CF_3CONH (CH_2)_5NH_2$, in anhydrous carbon tetrachloride.

3. The remainder of the nucleotide sequence of the oligonucleotide is produced in a two-step procedure in which the dimethoxytrityl residue [DMTr] is removed from the guanidine nucleotide now bound to the solid support ($Nu_2$ in the reaction scheme above) and the desired nucleotides A ($Nu_3$), C ($Nu_4$), C($Nu_5$) and so on up to G ($Nu_{17}$) (SEQ ID NO:4) are added stepwise (i.e., to the now free end of the dinucleoside which, for convenience, can be referred to as the 5' end using phosphoramidite or H-phosphonate chemistry resulting in molecule (IV).

4. The protecting group ($CO—CF_3$) present on $NH(CH_2)_6NH—CO—CF_3$ is removed during deprotection of oligonucleotides in aqueous ammonia for 6 hours at 55° C., resulting in production of a functionalized oligonucleotide (V) (in which the previously protected amino group is unprotected) of the desired sequence, in which there is an aminoalkylphosphoramidate residue of the formula:

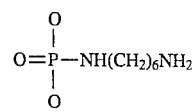

present at the desired internucleoside phosphate linkage(s).

5. The unbound modified oligonucleotide with the aminoalkylphosphoramidate residue is reacted with a non-radioactive material, such as biotin, fluorescein or rhodamine in appropriate form (e.g., N-hydroxysuccinimide ester of biotin, N-caproyl amidobiotin, fluorophore isothiocyanates), which becomes bound to the amino group of the aminoalkylphosphoramidate internucleoside linkage.

Alternatively, the following steps are carried out to produce a non-radioactively labelled oligonucleotide with a functionalized aminoalkylphosphotriester:

METHOD 2

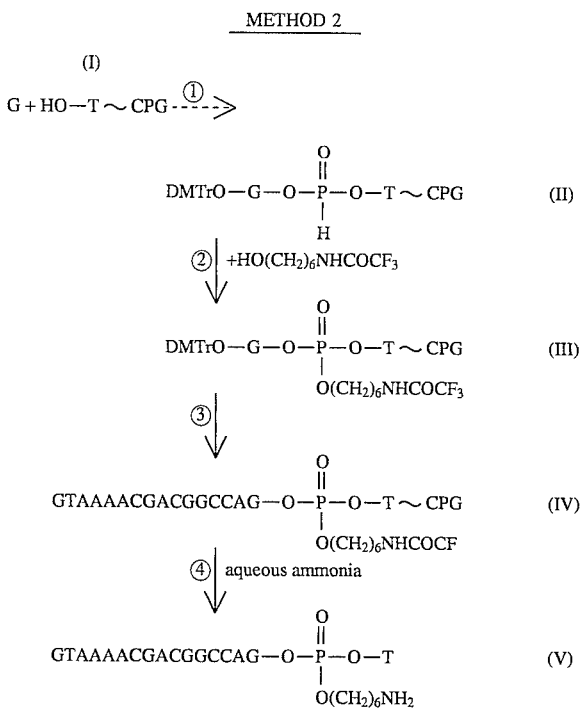

1. Initially, T ($Nu_1$) and G ($Nu_2$) are coupled as described in Uhlmann et al. (*Chem. Rev.* (1990) 90:551–552).

2. Oxidation is carried out using a protected amino alcohol such as FMOC—$NH(CH_2)_2OH$, FMOC—$NH(CH_2)_3OH$, FMOC—$NH(CH_2)_4OH$, FMOC—$NH(CH_2)_5OH$, or N-1-fluoroenylmethyoxcarbonylamino-hexanol (pentanol) (FMOC—$NH(CH_2)_6OH$) in the presence of N-methylimidazole-triethylamine-carbontetrachloride, resulting in the formation of a phosphotriester linkage between G and T.

3. The remainder of the nucleotide sequence of the oligonucleotide is covalently added using phosphoramidite, H-phosphonate, or methylphosphonoamidite chemistry as described by copending patent application entitled "METHOD OF SYNTHESIZING OLIGONUCLEOTIDES AND THEIR ANALOGS ADAPTABLE TO LARGE SCALE SYNTHESIS" (Ser. No. 07/334,679) and Uhlmann et al. (1990) *Chem. Rev.* 90:534–583).

4. After the oligonucleotide is produced, the protecting group on the primary aliphatic amino alcohol is removed, resulting in the production of functionalized oligonucleotide in which there is an aminoalkylphosphotriester residue present at the desired internucleoside phosphotriester linkage(s).

5. The unbound modified oligonucleotide with the aminoalkylphosphotriester residue in then reacted with biotin, fluoroscein, rhodamine, or derivatives thereof, or with any other non-radioactive labels capable of being bound to the amino group of the residue.

To prepare an oligonucleotide with a functionalized aminoalkylphosphorothioamidate, the method is carried out as follows:

METHOD 3

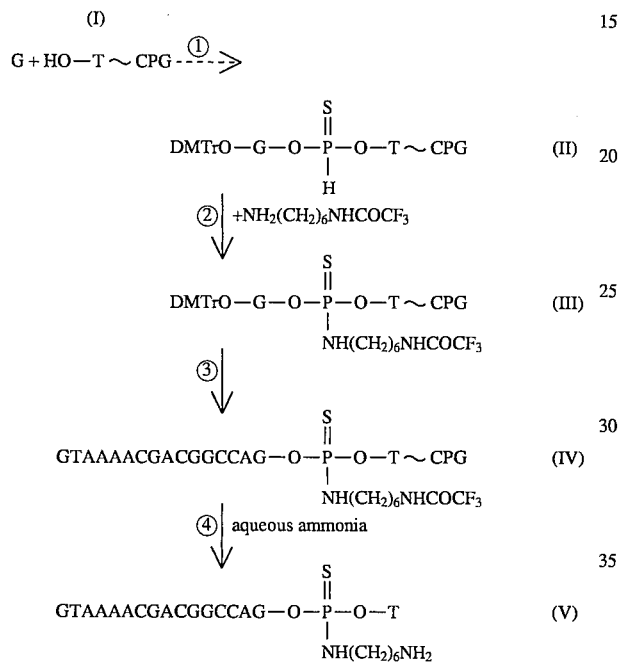

1. Initially, thymidine ($Nu_1$) and guanidine ($Nu_2$) (I) are coupled using art-recognized H-phosphonate chemistry, resulting in production of a support-bound dinucleoside H-phosphonate (II).

2. The support-bound dinucleoside H-phosphonate (II) is oxidized using 4% N-1-trifluoroacetyldiaminohexane ($NH(CH_2)_6NH$—CO—$CF_3$) in carbon tetrachloride-dioxane (8:2, volume/volume) for 30 minutes, resulting in formation of a phosphonothioate internucleoside linkage between $Nu_2$ and $Nu_1$ (III). In other tests, oxidation is carried out using $CF_3CONH(CH_2)_2NH_2$, $CF_3CONH(CH_2)_3NH_2$, $CF_3CONH(CH_2)_4NH_2$, or $CF_3CONH(CH_2)_5NH_2$ in anhydrous carbon tetrachloride.

3. The remainder of the nucleotide sequence of the oligonucleotide is produced in a two-step procedure in which the dimethoxytrityl residue [DMTr] is removed from the guanidine nucleotide now bound to the solid support ($Nu_2$ in the reaction scheme above) and the desired nucleotides A ($Nu_3$), C ($Nu_4$), C($Nu_5$) and so on up to G ($Nu_7$) (SEQ ID NO:4) are added stepwise (i. e., to the now free end of the dinucleoside which, for convenience, can be referred to as the 5' end using phosphoramidite or H-phosphonate chemistry resulting in molecule (IV).

4. The protecting group (CO—$CF_3$) present on $NH(CH_2)_6NH$—CO—$CF_3$ is removed during deprotection of oligonucleotides in aqueous ammonia for 6 hours at 55° C., resulting in production of a functionalized oligonucleotide (V) (in which the previously protected amino group is unprotected) of the desired sequence, in which there is an aminoalkylphosphorothioamidate residue of the formula:

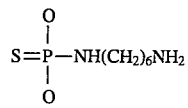

present at the desired internucleoside phosphate linkage(s).

5. The unbound modified oligonucleotide with the aminoalkylphosphorothioamidate residue is reacted with a non-radioactive material, such as biotin, fluorescein or rhodamine in appropriate form (e.g., N-hydroxysuccinimide ester of biotin, N-caproyl amidobiotin, fluorophore isothiocyanates), which becomes bound to the amino group of the aminoalkylphosphonothioate internucleoside linkage.

Other functionalized oligomers with 5, 17, 25, and 50 nucleotides are also prepared. All of these oligonucleotides are listed in TABLES 2A-2D below, where "↓" indicates the position of the functionalized residue.

TABLE 2A

| OLIGOMER # | SEQUENCE | SEQ ID NO: |
|---|---|---|
| 1 | AAATG | 1 |
| 2 | AAA↓TG | 1 |
| 3 | A↓AATG | 1 |
| 4 | AA↓AT↓G | 1 |
| 5 | A↓A↓A↓T↓G | 1 |
| 6 | CGGCA | 2 |
| 7 | CGG↓CA | 2 |
| 8 | C↓GGCA | 2 |
| 9 | CG↓G↓CA | 2 |
| 10 | C↓G↓G↓C↓A | 2 |
| 11 | UGCCA | 3 |
| 12 | UGC↓CA | 3 |
| 13 | U↓GCCA | 3 |
| 14 | UG↓CC↓A | 3 |
| 15 | U↓G↓C↓C↓A | 3 |

TABLE 2B

| OLIGOMER # | SEQUENCE | SEQ ID NO: |
|---|---|---|
| 16 | GTAAAACGACGGCCAGT | 4 |
| 17 | GTAAAACGACGGCCAG↓T | 4 |
| 18 | GTAAAACG↓ACGGCCAGT | 4 |
| 19 | G↓TAAAACGACGGCCAG↓T | 4 |
| 20 | G↓T↓A↓A↓A↓A↓C↓G↓A↓C↓G↓G↓C↓C↓A↓G↓T | 4 |

TABLE 2B-continued

| OLIGOMER # | SEQUENCE | SEQ ID NO: |
|---|---|---|
| 21 | GTATTCAAAGGAGTACC | 5 |
| 22 | GTATTCAAAGGAGTAC↓C | 5 |
| 23 | GTATTCAA↓A↓GGAGTACC | 5 |
| 24 | G↓TATTCA↓AAGGA↓GTAC↓C | 5 |
| 25 | G↓T↓A↓T↓T↓C↓A↓A↓A↓G↓G↓A↓G↓T↓A↓C↓C | 5 |
| 26 | GAGCAUCACGGUGAGCG | 6 |
| 27 | GAGCAUCACGGUGAGC↓G | 6 |
| 28 | GAGCAUCA↓C↓GGUGAGCG | 6 |
| 29 | G↓AGCA↓UCACGGUG↓AGC↓G | 6 |
| 30 | G↓A↓G↓C↓A↓U↓C↓A↓C↓G↓G↓U↓G↓A↓G↓C↓G | 6 |

TABLE 2C

| OLIGOMER # | SEQUENCE | SEQ ID NO: |
|---|---|---|
| 31 | CTCTCGCACCCATCTCTCTCCTTCT | 7 |
| 32 | CTCTCGCACCCATCTCTCTCCTTC↓T | 7 |
| 33 | CTCTCGCACCC↓A↓T↓CTCTCTCCTTCT | 7 |
| 34 | CT↓CTCGCACCCAT↓C↓TCTCTCCTT↓CT | 7 |
| 35 | C↓T↓C↓T↓C↓G↓C↓A↓C↓C↓C↓A↓T↓C↓T↓C↓T↓C↓T↓C↓C↓T↓T↓C↓T | 7 |
| 36 | GAATGACTGATTGAGTGACTGAATG | 8 |
| 37 | GAATGACTGATTGAGTGACTGAAT↓G | 8 |
| 38 | GAATGACTGA↓T↓TGAGTGACTGAATG | 8 |
| 39 | GAATGA↓CTGA↓T↓TGAGTGAC↓TGAAT↓G | 8 |
| 40 | G↓A↓A↓T↓G↓A↓C↓T↓G↓A↓T↓T↓G↓A↓G↓T↓G↓A↓C↓T↓G↓A↓A↓T↓G | 8 |
| 41 | CAGUGACUGACUGAGCGACUGAACU | 9 |
| 42 | CA↓GUGACUGACUGAGCGACUGAACU | 9 |
| 43 | CAGUGACUGA↓C↓UGAGCGACU↓GAACU | 9 |
| 44 | CA↓GUG↓ACU↓GACUGAGC↓G↓ACUGAA↓CU | 9 |
| 45 | C↓A↓G↓U↓G↓A↓C↓U↓G↓A↓C↓U↓G↓A↓G↓C↓G↓A↓C↓U↓G↓A↓A↓C↓U | 9 |

TABLE 2D

| OLIGOMER # | SEQUENCE | SEQ ID NO: |
|---|---|---|
| 46 | CGATGCGTAGGCCTAGAACTGGACTTACACTGGGATGCAAGTCAGCTGAT | 10 |
| 47 | CG↓ATGCGTAGGCCTAGAACTGGACTTACACTGGGATGCAAGTCAGCTGAT | 10 |
| 48 | C↓GATGCGTAG↓GCCTAGAACTGGACT↓TA↓CACTGGGATGCAAGTCAGCTGAT | 10 |
| 49 | CG↓ATG↓CGTAGGCCTAGA↓ACT↓G↓GACTTACACTGGGATGCA↓AG↓TCAGCTGAT | 10 |
| 50 | C↓G↓A↓T↓G↓C↓G↓T↓A↓G↓G↓C↓C↓T↓A↓G↓A↓A↓C↓T↓G↓G↓A↓C↓T↓T↓A↓C↓A↓C↓T↓G↓G↓G↓A↓T↓G↓C↓A↓A↓G↓T↓C↓A↓G↓C↓T↓G↓A↓T | 10 |
| 51 | TCAGTCGAGAGCTCGAGCTCGAGCGCTAGCGATGCAGTGCGATCGATAGC | 11 |
| 52 | T↓CAGTCGAGAGCTCGAGCTCGAGCGCTAGCGATGCAGTGCGATCGATAGC | 11 |
| 53 | TCAGTCGAGAGCTCGAGCTCGAGCTAGC↓G↓A↓TGC↓AGTGCGATCGATAGC | 11 |
| 54 | TCAG↓TCGAGAGC↓TCGAGCTCGAGCGC↓T↓AGCGAT↓GCAGTGCG↓ATCGATAGC | 11 |
| 55 | T↓C↓A↓G↓T↓C↓G↓A↓G↓A↓G↓C↓T↓C↓G↓A↓G↓C↓T↓C↓G↓A↓G↓C↓G↓C↓T↓A↓G↓C↓G↓A↓T↓G↓ C↓A↓G↓T↓G↓C↓G↓A↓T↓C↓G↓A↓T↓A↓G↓C | 11 |
| 56 | AGCGCACUAGGCAAGUCCGCGAGAUCCACGAGCCAAUACGGACUCGCAGA | 12 |
| 57 | AGCGCACUAGGCAAGUCCGCGAGAUCCACGAGCCAAUACGGACUCGCA↓GA | 12 |
| 58 | AGCGCACUAGGCAAGUC↓C↓G↓CGAGAUCCACGAGCCAAUACGGACUCGCAGA | 12 |
| 59 | AGC↓GCACUAGGCAA↓GUCCGCGAGAUCCACGAGC↓CAAUACGGA↓C↓UCGCAGA | 12 |
| 60 | A↓G↓C↓G↓C↓A↓C↓U↓A↓G↓G↓C↓A↓A↓G↓U↓C↓C↓G↓C↓G↓A↓G↓A↓U↓C↓C↓A↓C↓G↓A↓G↓C↓ C↓A↓A↓U↓A↓C↓G↓G↓A↓C↓U↓C↓G↓C↓A↓G↓A↓ | 12 |

4. Characterization of the Functionalized Oligomers

Assessment of the oligomers is carried out by analytical ion exchange high pressure liquid chromatography (HPLC). For example, when oligomer 17 (SEQ ID NO:4) is analyzed, a major peak is seen eluting earlier than that of a similar but unfunctionalized oligomer (oligomer 16, (TABLE 2) SEQ ID NO:4) with the same gradient (FIGS. 1A and 1B), confirming that in the oligomer 17, one of the internucleoside linkages is a phosphoramidate linkage, which is non-ionic at phosphorous. Oligomers 18 and 19 (both SEQ ID NO:4) which are functionalized at different sites, also show a HPLC profile similar to that of oligomer 17. Oligomer 19, which is functionalized at two sites, elutes even earlier (FIG. 1A, chromatograph (c)).

Figure 1A:
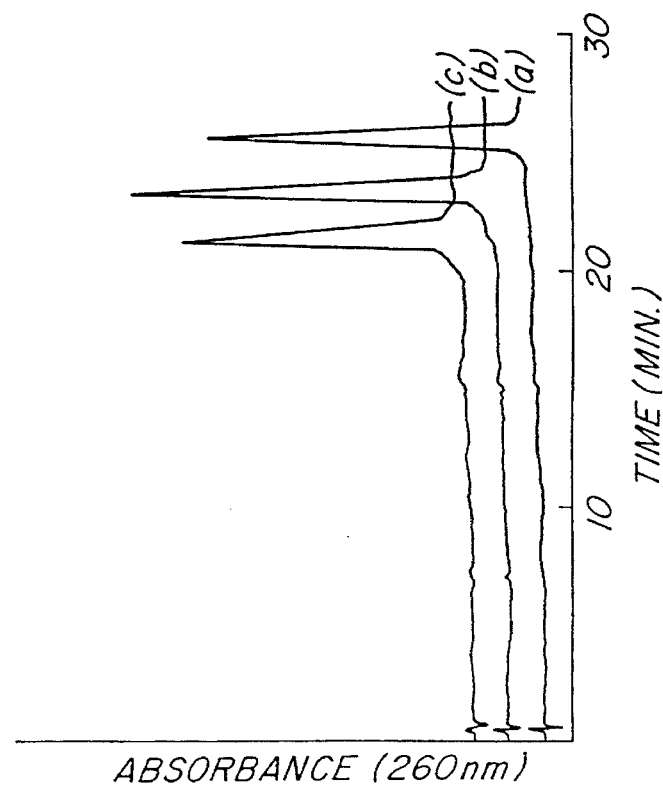
FIG. 1A is a graphic representation of the results of analytical ion exchange HPLC of oligomers 1 (chromatograph (a)), 2 (chromatograph (b)), and 5 (chromatograph (c))

When ion exchange HPLC purified oligomer 17 is analyzed by reversed phase HPLC, it gives a doublet peak in ratio of 1:2 (FIG. 1A, chromatograph (e)) compared to oligomer 16 (FIG. 1A, chromatograph (d)). These results are due to the diastereoisomeric nature of phosphoramidate internucleoside linkage. Similarly, oligomer 19 elutes as a broad peak because of two such diastereoisomeric linkages (FIG. 1F). Both oligomers 17 and 19 have retention times longer than that of oligomer 16 because of the hydrophobic nature of the alkyl chain present in oligomers 17 and 19.

Figure 2A:
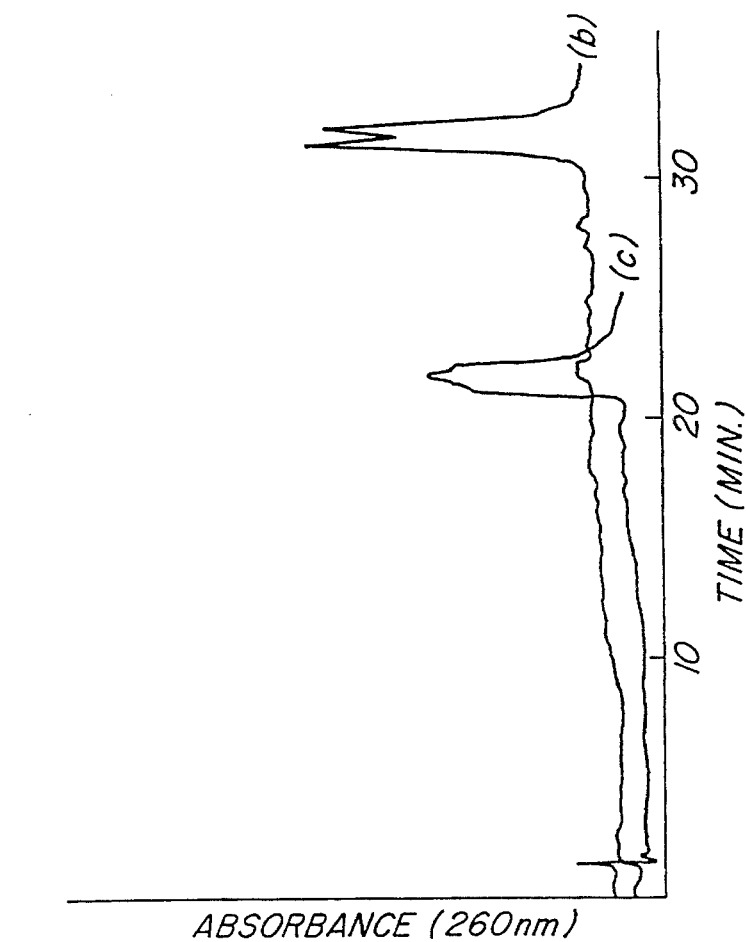
FIG. 2A is a graphic representation of the results of reversed phase HPLC traces of oligomer 2 (chromatogram (a)), and reaction mixture of oligomer with biotin N-hydroxysuccinimide (chromatograph (b))
Figure 2B:
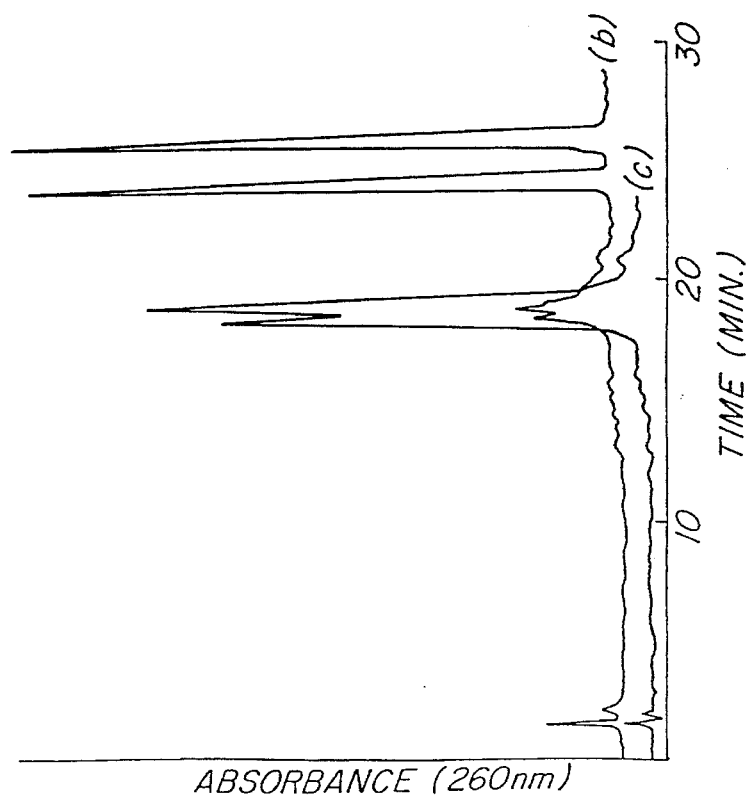
FIG. 2B is a graphic representation of the results of reversed phase HPLC traces of oligomer 5 (chromatograph (c)) and reaction mixture of oligomer 5 with biotin N-hydroxysuccinimide (chromatograph (d)).

Reaction of the oligomers is carried out with biotin N-hydroxysuccinimide using reported conditions (Agrawal et al. (1986) *Nucl. Acid Res.* 14:6227–6245). For example, the reaction mixture after gel filtration (Sephadex G-25) of oligomer 6 shows two new peaks of the diastereomeric biotin adducts (FIG. 2A, chromatograph (b)). Similarly, reaction of oligomer (15) gives a broad peak as a doublet eluting later than the unreacted material (FIG. 2B, chromatographs (c) and (d)).

Thus, the method described herein provides a way for functionalizing DNA and/or RNA containing oligonucleotides of any sequence and internucleotide linkage at one or more specified sites.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A compound consisting of a range of five to fifty covalently linked nucleosides wherein at least one linkage between the nucleosides is through an aminoalkylphosphotriester residue having the structure:

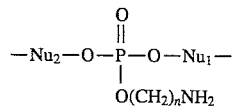

wherein n is 2 to 6, and $Nu_1$ and $Nu_2$ are those nucleosides adjacent said residue.

2. The compound according to claim 1, wherein the nucleosides are selected from the group consisting of adenosine, thymidine, cytidine, guanoside, and uridine.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

A A A T G        5

( 2 ) INFORMATION FOR SEQ ID NO:2:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:2:

C G G C A        5

( 2 ) INFORMATION FOR SEQ ID NO:3:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: YES ( x i ) SEQUENCE DESCRIPTION: SEQ ID NO:3:

U G C C A        5

( 2 ) INFORMATION FOR SEQ ID NO:4:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

GTAAAACGAC GGCCAGT                                      17

(2) INFORMATION FOR SEQ ID NO:5:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:5:

GTATTCAAAG GAGTACC                                      17

(2) INFORMATION FOR SEQ ID NO:6:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:6:

GAGCAUCACG GUGAGCG                                      17

(2) INFORMATION FOR SEQ ID NO:7:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:7:

CTCTCGCACC CATCTCTCTC CTTCT                             25

(2) INFORMATION FOR SEQ ID NO:8:

(i) SEQUENCE CHARACTERISTICS:
    (A) LENGTH: 25 base pairs
    (B) TYPE: nucleic acid (C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:8:

GAATGACTGA TTGAGTGACT GAATG                               25

(2) INFORMATION FOR SEQ ID NO:9:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:9:

CAGUGACUGA CUGAGCGACU GAACU                               25

(2) INFORMATION FOR SEQ ID NO:10:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:10:

CGATGCGTAG GCCTAGAACT GGACTTACAC TGGGATGCAA GTCAGCTGAT    50

(2) INFORMATION FOR SEQ ID NO:11:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: cDNA (iii) HYPOTHETICAL: YES (iv) ANTI-SENSE: YES (xi) SEQUENCE DESCRIPTION: SEQ ID NO:11:

TCAGTCGAGA GCTCGAGCTC GAGCGCTAGC GATGCAGTGC GATCGATAGC    50

(2) INFORMATION FOR SEQ ID NO:12:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:12:

AGCGCACUAG GCAAGUCCGC GAGAUCCACG AGCCAAUACG GACUCGCAGA 50